United States Patent [19]

Faulds et al.

[11] Patent Number: 5,252,328

[45] Date of Patent: * Oct. 12, 1993

[54] MYCOPLASMA HYOPNEUMONIAE ANTIGEN AND USES THEREFOR

[75] Inventors: Daryl Faulds, Millbrae; Mimi Vishoot, San Francisco; Emily Brooks, Pacifica, all of Calif.

[73] Assignee: Martin Marietta Energy Systems, Inc., Oak Ridge, Tenn.

[*] Notice: The portion of the term of this patent subsequent to Aug. 31, 2010 has been disclaimed.

[21] Appl. No.: 335,726

[22] Filed: Apr. 7, 1989

Related U.S. Application Data

[63] Continuation-in-part of Ser. No. 30,130, Mar. 26, 1987, abandoned.

[51] Int. Cl.$^5$ .............................................. A61K 39/02
[52] U.S. Cl. ...................................... 424/92; 424/88; 435/870; 530/350; 530/806; 530/820; 530/821
[58] Field of Search ................... 424/92, 88; 435/870; 530/350, 806, 820, 821

[56] References Cited

U.S. PATENT DOCUMENTS 4,894,332 1/1990 Schaller et al. ..................... 424/92

FOREIGN PATENT DOCUMENTS 0196215 1/1986 European Pat. Off. .

OTHER PUBLICATIONS

Wise et al, *Chemical Abstracts*, vol. 107, reference #196101d, 1987.
Schaller et al, *Chemical Abstracts*, vol. 106, reference #143977s, 1987.
Young et al, *Chemical Abstracts*, vol. 106, Reference #212183y, 1987.
Klinkert et al, *Chemical Abstracts*, vol. 103, reference #103070x, 1985.
Ross et al, *Amer. J. Vet. Ren.* vol. 45, No. 10, pp. 1899-1905, 1984.

Primary Examiner—Michael G. Wityshyn
Assistant Examiner—Abdel A. Mohamed
Attorney, Agent, or Firm—Ivan L. Ericson; Harold W. Adams

[57] ABSTRACT

A composition for protecting swine against mycoplasmal pneumonia caused by *M. hyopneumoniae* which includes at least one protein which is an *M. hyopneumoniae* antigen. The *M. hyopneumoniae* antigen is present in an amount effective for protection of swine against mycoplasmal pneumonia caused by *M. hyopneumoniae*. A preferred antigen is the *M. hyopneumoniae* 74.5 kda antigen.

6 Claims, No Drawings

MYCOPLASMA HYOPNEUMONIAE ANTIGEN AND USES THEREFOR

This application is a continuation-in-part of application Ser. No. 030,130, filed Mar. 26, 1987, now abandoned.

This invention relates to *Mycoplasma hyopneumoniae* (*M. hyopneumoniae*) and more particularly to *Mycoplasma hyopneumoniae* antigens. Still more particularly, this invention relates to a vaccine for protecting against mycoplasmal pneumonia, and in particular mycoplasmal pneumonia of swine.

The disease caused by *Mycoplasma hyopneumoniae* (in particular in swine), occurs throughout the world and is a disease associated with the loss of swine. The disease generally results in inefficient, stunted and sickly animals, and effected swine are often prone to secondary infection by opportunistic microorganisms.

There have been numerous attempts to provide a vaccine for protecting swine against mycoplasmal pneumonia; however, such vaccines have not been successful.

Kristensen et al. in *Am. J. Vet. Res.* 42 (1981) page 784, found no protection of swine against mycoplasmal pneumonia after injection with heat inactivated cells of *Mycoplasma hyopneumoniae*.

Etheride, et al *Res. Vet. Sci.* 33 (1982) page 188 found incomplete protection against lung and colonization by Mycoplasma when a live vaccine was given intravenously, subcutaneously or intraperitoneally.

Ross et al. *Am. J. Vet Res.* 45 (1984) page 1899 disclosed that the use of *Mycoplasma hyopneumoniae* extracts prepared by a freeze thaw procedure provided only variable protection and, in some instances, enhanced lesion development. Ross et al. also claimed that injection of such agent into swine gave some level of protection against an intratrachael challenge exposure consisting of 4 ml of supernatant from a 10% suspension of pneumonic lung containing strain VPP-11 combined with 1 ml of a 24 hour culture of 15 to 20 passage of the same strain.

As a result, to date, an effective vaccine for protecting swine against mycloplasmal pneumonia has not been developed.

In accordance with one aspect of the present invention, there is provided a vaccine and a method for protection against mycoplasmal pneumonia, and in particular mycoplasmal pneumonia of swine.

More particularly, in accordance with one aspect of the present invention, there is provided a vaccine for protecting against mycoplasmal pneumonia which includes one or more *Mycoplasma hyopneumoniae* antigens or fragments thereof wherein the *Mycoplasma hyopneumoniae* antigens and/or fragments thereof are essentially free of materials which possess immunosuppressive activity. A vaccine which is essentially free of materials which possess immunosuppressive activity lacks immunosuppressive activity.

Applicant has found that *Mycoplasma hyopneumoniae* organisms include a plurality of antigens, some of which have immunosuppressive activity and some of which lack immunosuppressive activity. Applicant has further found that by using essentially only the *Mycoplasma hyopneumoniae* antigens and/or fragments of such antigens which lack immunosuppressive activity in a vaccine, such vaccine may be effectively employed for protection against mycoplasmal pneumonia, and in particular for protection against mycoplasmal pneumonia in swine.

For example, a procedure for determining whether or not a compound or composition possesses immunosuppressive activity is reported in Suter, M., Kobisch, M. and J. Nicolet (1985). *Infect. and Immun.*, Vol. 49, page 615, "Stimulation of immunoglobulin containing cells and isotype specific antibody response in experimental *Mycoplasma hyopneumoniae* infection in specific-pathogen-free pigs. A preferred procedure is reported in Example 3.

The *Mycoplasma hyopneumoniae* antigens which are employed in the vaccine may be obtained from *Mycoplasma hyopneumoniae* organisms and in particular from the membrane of *Mycoplasma hyopneumoniae* organisms. As hereinabove indicated, the *Mycoplasma hyopneumoniae* organisms and, in particular, the membrane of the *Mycoplasma hyopneumoniae* organism contains both antigens which have immunosuppressive activity and antigens which do not have immunosuppressive activity; accordingly, in obtaining the antigens for the vaccine it is necessary to selectively recover the *Mycoplasma hyopneumoniae* antigens which lack immunosuppressive activity.

In accordance with one method, the membrane of the *Mycoplasma hyopneumoniae* organism may be treated with a mild detergent, and in particular a non-ionic detergent to produce both a soluble and insoluble fraction. Applicant has found that the insoluble fraction includes *Mycoplasma hyopneumoniae* antigens which lack immunosuppressive activity, whereas the soluble fraction, obtained by treatment with a mild detergent, includes *Mycoplasma hyopneumoniae* antigens which lack immunosuppressive activity, as well as materials which have immunosuppressive activity. The insoluble fraction obtained by treating the membrane from *Mycoplasma hyopneumoniae* organism with a mild detergent may be employed for formulating a vaccine for protecting animals against mycoplasmal pneumonia or, alternatively, the soluble fraction may be treated to remove materials which have immunosuppressive activity, whereby such fraction may be used in formulating a vaccine.

As a further alternative, the membrane derived from *Mycoplasma hyopneumoniae* organism may be treated with other agents to selectively solubilize the surface antigens which possess immunosuppressive activity and thereby provide an insoluble fraction containing *Mycoplasma hyopneumoniae* antigen(s) which lack immunosuppressive activity. As representative examples of other solubilizing agents, there may be mentioned: n-octyglucoside; sodium deoxycholate; CHAPS (3-[(3-Cholamidopropyl)dimethylammonio]1-propane sulfonate, etc.

As another example of a procedure for obtaining *Mycoplasma hyopneumoniae* antigens which lack immunosuppressive activity for use in production of a vaccine for protecting against mycoplasmal pneumonia, there may be mentioned electrophoretic procedures for separating the various *Mycoplasma hyopneumoniae* membrane antigens so as to obtain one or more *Mycoplasma hyopneumoniae* antigens which lack immunosuppressive activity.

The above procedures and other should be apparent to those skilled in the art from the teachings herein.

The *Mycoplasma hyopneumoniae* antigens which lack immunosuppressive activity and which are employed for formulating a vaccine for protecting against mycoplasmal pneumonia generally have a molecular weight of at least 10 Kda and generally no greater than 350 Kda. In most cases, such antigens have a molecular weight of from 22 Kda to 121 Kda. The vaccine may include one or more of such antigens or fragments thereof. As should be apparent, a fragment would have a molecular weight lower than the antigen from which it is derived. In an embodiment, the vaccine contains one or more of the antigens having the following molecular weights: 22.5 Kda; 34 Kda; 36 Kda; 41 Kda; 44 Kda; 48 Kda; 52 Kda; 64 Kda; 74.5 Kda; 79 Kda; 88.5 Kda; 96.5 Kda and 121 Kda. Most preferably, the vaccine contains one or more of the 36 Kda, 48 Kda, 64 Kda, 74.5 Kda, 79 Kda, 88.5 Kda, and 96 Kda antigens. It is to be understood that it is possible within the spirit and scope of the present invention to use one or more of such antigens in formulating the vaccine and/or to use fragments thereof. In one embodiment, a vaccine is formulated from a mixture of such antigens. It is also possible to use other antigens having the hereinabove described characteristics.

The molecular weights for characterizing the antigen(s) are obtained by discontinuous polyacrylamide gel electrophoresis using the SDS buffer system described by Laemmli, *Nature* 227; 680-85 (London 1970) with an acrylamide concentration of 12% and a bis-acrylamide to acrylamide ratio of 0.8:30.

The non-ionic detergent is employed in amounts which are sufficient to solubilize the *Mycoplasma hyopneumoniae* antigens which possess immunosuppressive activity, without solubilizing the *Mycoplasma hyopneumoniae* antigens which lack immunosuppressive activity. In general, the weight ratio of non-ionic detergent to *Mycoplasma hyopneumoniae* organism portion which is subjected to treatment is from 10 to 1 to about 0.05 to 1, and preferably from about 5.0 to 1 to 0.5 to 1. The treatment is generally effected at a temperature which does not exceed 40° C., with the temperature most generally being in the order of from 0° C. to 37° C.

The treatment is for a time sufficient to effect solubilization of the *Mycoplasma hyopneumoniae* antigens which possess immunosuppressive activity, and in general, such time is in the order of from 0.5 to 12 hours; however, in some cases, longer or shorter times may be employed.

The solution employed to solubilize the antigen(s) generally has an ionic strength of from 0.05 to 1.0M salt. A preferred solubilizing agent contains 0.2M sodium ion.

As hereinabove indicated, in general, the membrane of the *Mycoplasma hyopneumoniae* organism is subject to such treatment. Such membrane may be obtained by disrupting the organism by procedures generally known in the art, such as a freeze-thaw cycle; sonication; etc. Alternatively, the antigen(s) may be derived from the whole organism. The selection of a suitable procedure is deemed to be within the scope of those skilled in the art from the teachings herein.

Although the present invention has been particularly described with respect to obtaining *Mycoplasma hyopneumoniae* antigens which lack immunosupressive activity by treating *Mycoplasma hyopneumoniae* organisms, it is to be understood that *Mycoplasma hyopneumoniae* antigens lacking immunosupressive activity may be obtained by other procedures, such as genetic engineering. Thus, the scope of the present invention is not limited to the described embodiment for obtaining such antigen(s).

Similarly, it is possible within the spirit and scope of the present invention to employ a fragment of one or more of the hereinabove described antigens in producing a vaccine of the present invention in place of or in conjunction with one or more of such antigens. The term fragment of the antigen as used herein is a fragment of the antigen which (1) includes an epitope which will produce an antibody which is recognized by such antigen and (2) will immunoreact with serum of an animal (in particular swine) convalescing from mycoplasmal pneumonia.

A vaccine for protection against mycoplasmal pneumonia, and in particular for protecting swine against mycoplasmal pneumonia, is comprised of one or more *Mycoplasma hyopneumoniae* antigens which lack immunosuppressive activity or fragments thereof, as hereinabove described, in combination with a suitable physiologically acceptable carrier. Such *Mycoplasma hyopneumoniae* antigens and/or fragments are employed in the vaccine in an amount effective to provide protection against mycoplasmal pneumonia.

In general, the vaccine contains at least 5 micrograms per dose and preferably at least 100 micrograms per dose of such antigen(s) and/or fragments of the antigen. In most cases, the vaccine does not include such antigen(s) and/or fragments in an amount greater than 20 milligrams.

If multiple doses are employed, in general, the vaccine would not be administered in an amount which exceeds three doses over eight weeks.

The term "protection" or "protecting" when used with respect to the vaccine for mycoplasmal pneumonia described herein means that the vaccine prevents mycoplasmal pneumonia and/or reduces the severity of mycoplasmal pneumonia.

The carrier which is employed in conjunction with the protein antigen and/or fragments may be any one of a wide variety of carriers. As representative examples of suitable carriers, there may be mentioned: mineral oil, alum, synthetic polymers, etc. Carriers for vaccines are well known in the art and the selection of a suitable carrier is deemed to be within the scope of those skilled in the art from the teachings herein. The selection of a suitable carrier is also dependent upon the manner in which the vaccine is to be administered. The vaccine may be in the form of an injectable dose and may be administered intra-muscularly, intravenously, or by sub-cutaneous administration. It is also possible to administer the vaccine orally by mixing the active components with feed or water; providing a tablet form, etc. Other means for administering the vaccine should be apparent to those skilled in the art from the teachings herein; accordingly, the scope of the invention is not limited to a particular delivery form.

It is also to be understood that the vaccine may include active components or adjuvants (e.g., Freund's incomplete adjuvant) in addition to the antigen(s) or fragments hereinabove described.

The vaccine is generally employed in non-human animals which are susceptible to mycoplasmal pneumonia, and in particular swine, and bovines.

The present invention will be further described with respect to the following examples; however, the scope of the invention is not to be limited thereby.

EXAMPLE 1

Extraction of Surface Proteins

*Mycoplasma hyopneumoniae* is grown in Friis medium to a density of approximately $10^9$ to $10^{10}$ color changing units per milliliter. The cells are harvested by centrifugation and washed four times with phosphate buffered saline. The cells are lysed in 10 mM Tris 10 mM EDTA by repeated freeze thaw cycles in which the cells are transferred alternately between a dry-ice ethanol bath and a 37° C. bath with constant mixing. Insoluble components and unlysed cells are removed by high speed centriguation. The membranes left in suspension are harvested by ultra-high speed centrifugation (33,000 g for 45 minutes), washed in phosphate buffered saline, and solubilized by Triton X-100 phosphate buffered saline solution. At this point, the Triton-soluble and Triton-insoluble components may be separated by ultra-high speed centrifugation (100,000 g for 45 minutes. The Triton insoluble fraction consists of many of the same proteins as the Triton-soluble fraction.

The specific protective antigens in the insoluble fraction were identified by indirect enzyme-linked immunoassay. Proteins of *Mycoplasma hyopneumoniae* which make up the protective fraction were separated by SDS-polyacrylamide gel electrophoresis and transferred to a nitrocellulose sheet by blotting. Sera obtained from convalescent pigs were then incubated with the nitrocellulose sheets and the immuno-reactive proteins recognized by biotinylated goat antisera prepared against pig antibodies. The recognized antigens were identified by their subsequent reaction with an avidin-biotin peroxidase conjugate which causes a color to develop at the bound protein.

The immuno-reactive proteins which make up the protective fraction were characterized as to their approximate molecular weights by SDS, 12% polyacrylamide-gel electrophoresis. They include: 22.5, one or more of 34, one or more of 36, 41, 44, 48, 52, 64, 68, 74.5, 79, 88.5, 96.5, and 121 kilo-Dalton components.

The 34 kDa component has a sequence of amino acid residues in its amino terminus which consists of:

Met-Lys-Pro-Ile - - -
Ile-Ala-Leu-Ile-Gly-Ala-Asn-Val-Val - - - Phe

The 36 kDa component has a sequence of amino acid residues in its amino terminus which consists of:

¹Met-Ala-Asn-Ser-Asp-Lys-Ile-Ala-Leu-Asn-Asn-
Ile-Gly-Ala

The 41 kDa component has a sequence of amino acid residues in its amino terminus which consists of:

1
Met-Asp-Lys-Phe-Arg-Tyr-Val-Lys-Pro-Gly-
Gln-Ile-Met-Ala-Lys-Asp-Glu-Glu-Met-Ile-Arg-
Phe-Leu-Asp-Ile-Asp-Gly-Asn-Leu-Leu

The 44 kDa component has a sequence of amino acid residues in its amino terminus which consists of:

Ala-Gly-Asn-Gly-Gln-Thr-Glu-Ser-Gly - - - Gln-Ile
- - - Lys

The 48 kDa component has a sequence of amino acid residues in its amino terminus which consists of:

Ala-Lys-Ile-Thr-Thr-Glu-Gly-Lys-Lys-Asp-Phe - - -
Arg-Ser-Lys

The 64 kDa component has a sequence of amino acid residues in its amino terminus which consists of:

Met-Lys-Leu-Ala-Lys-Leu-Leu-Lys - - -
Pro-Phe-Val-Leu-Lys-Ile

The 68 kDa component has a sequence of amino acid residues in its amino terminus which consists of:

Ala-Lys-Glu-Ile-Ile-Leu-Gly-Ile-Asp-Leu-Gly-Thr-
Asp-Asn-Ser-Val

The 74.5 kDa component has a sequence of amino acid residues in its amino terminus which consists of:

Met-Ala-Lys-Glu-Ile-Ile-Leu-Gly-Ile-Asp-Leu-Gly-
Thr-Thr-Asn-Ser-Val-Val-Ala-Ile-Ile-Glu-Asn-
Gln-Lys-Pro-Val-Val-Leu

The 79 kDa component has a sequence of amino acid residues in its amino terminus which consists of:

Ser - - - Lys-Leu-Val-Leu-Ala

The 88.5 kDa component has a sequence of amino acid residues in its amino terminus which consists of:

Gln-Glu-Asn-Leu-Asp-Asn-Ser-Gln-Asn

The 96 kDa component has a sequence of amino acid residues in its amino terminus which consists of:

Ala-Asp-Glu-Lys-Thr-Ser - - -
Gln-Lys-Asp-Pro-Ser-Thr-Leu-Arg-Ala-Ile-Asp-
Phe-Glu-Tyr-Asp-Glu-Asn-Thr

The 121 kDa component has a sequence of amino acid residues in its amino terminus which consists of:

Met-Lys-Asn-Lys-Lys-Ser-Thr-Leu-Lys - - -
Ala-Thr-Ala

EXAMPLE 2

A vaccine is prepared by aliquoting the insoluble fraction obtained in Example 1 into two doses of 1.7 ml and four doses of 2.0 ml, and each aliquot is homogenized with an equal volume of mineral oil adjuvant immediately prior to use.

The vaccine is administered to swine subcutaneously as follows:

1.7 ml aliquot vaccine at the age of seven weeks and booster injections of the 2.0 ml aliquot vaccine at two weeks and eight weeks after the initial injection.

EXAMPLE 3

In this assay specific-pathogen-free piglets are vaccinated with a test vaccine and a placebo. At weekly intervals equal numbers of piglets from each group are anesthetized and slaughtered. Bronchial or retropharyngeal lymph nodes are removed, fixed in paraformaldehyde, and embedded in paraffin. Sections are processed for immunohistology by incubation with rabbit anti-pig IgA, anti-pig IgM, and anti-pig IgG. The sections a e washed and further incubated sequentially with biotinylated goat anti-rabbit IgG, a commercially available avidin-biotinylated peroxidase complex, and a chromogenic substrate, such as 4-chloro-1-naphthol or diaminobenzidine. The number of stained (immunoglobulin-containing) cells per 100 mm² tissue section is determined for both the vaccinated and the control animals. A vaccine is immunosuppressive when the number of immunoglobulin containing cells in the retropharyngeal or bronchial lymph nodes is significantly lower than in control animals, as assessed by the immunohistological assay.

EXAMPLE 4

Piglets taken by Caesarean section were divided randomly into a vaccination group and a control group. The vaccination group received vaccines containing the 74.5 Kda antigen obtained according to the procedure of Example 1, whereas the control group received no vaccine.

The vaccination group received a subcutaneous injection in the leg of 100 ug of the 74.5 Kda antigen in Freund's incomplete adjuvant at 1 week of age. A booster injection was given, again of 100 ug of 74.5 Kda antigen in a suitable carrier, in the opposite leg, to the vaccination group, at 3 weeks. At 8 weeks, both groups were challenged with a transtracheal inoculation of $10^6$ CCU of *Mycoplasma hyopneumoniae*. At week 12, the piglets in both groups were killed and necropsy was undertaken.

In the control group, 5 out of 5 piglets were found to have a lung lesion score greater than 5%. The mean severity for the control group was 12.4% of lung surface effected, ±4.7%. In the vaccination group, only one piglet out of 4 had a lung lesion score greater than 5%. The mean severity was 4.2% of the lung surface effected, ±4.9%.

Numerous modifications and variations of the present invention are possible in light of the above teachings and, therefore, within the scope of the appended claims, the invention may be practiced otherwise than as particularly described.

What is claimed is:

1. A composition comprising:
   at least one protein; and a vehicle for said at least one protein, said at least one protein being an *M. hyopneumoniae* antigen, having a molecular weight of 74.5 Kda, said at least one protein being present in an amount effective for protection of swine against mycoplasmal pneumonia caused by *M. hyopneumoniae*.

2. The composition of claim 1 wherein said composition comprises at least 5 micrograms of said at least one protein per dose.

3. The composition of claim 2 wherein said composition comprises at least 100 micrograms of said at least one protein per dose.

4. A method of protecting swine against mycoplasmal pneumonia caused by *M. hyopneumoniae*, comprising:
   administering to swine an effective amount of at least one protein, said at least one protein being an *M. hyopneumoniae* antigen having a molecular weight of 74.5 Kda.

5. The method of claim 4 wherein said at least one protein is administered in an amount of at least 5 micrograms per dose.

6. The method of claim 5 wherein said at least one protein is administered in an amount of at least 100 micrograms per dose.

* * * * *

UNITED STATES PATENT AND TRADEMARK OFFICE
CERTIFICATE OF CORRECTION

PATENT NO. : 5,252,328
DATED : October 12, 1993
INVENTOR(S) : Daryl Faulds et al.

It is certified that error appears in the above-indentified patent and that said Letters Patent is hereby corrected as shown below:

On the cover page in Item [73] Assignee should read,
--ML Technology Ventures, L.P., New York, NY--.

and under OTHER PUBLICATIONS,

Attorney, Agent, or Firm should read, --Elliot M. Olstein; Raymond J. Lillie--.

Signed and Sealed this

Fifth Day of April, 1994

Attest:

BRUCE LEHMAN

*Attesting Officer*  *Commissioner of Patents and Trademarks*